(12) United States Patent
Philipps (10) Patent No.: US 10,751,160 B2
(45) Date of Patent: Aug. 25, 2020

(54) REMOVABLE ANCHORED LUNG VOLUME REDUCTION DEVICES

(71) Applicant: Spiration, Inc., Redmond, WA (US)

(72) Inventor: Alyssa Philipps, Seattle, WA (US)

(73) Assignee: Gyrus ACMI, Inc., Southborough, MA (US)

( * ) Notice: Subject to any disclaimer, the term of this patent is extended or adjusted under 35 U.S.C. 154(b) by 0 days.

(21) Appl. No.: 15/882,565

(22) Filed: Jan. 29, 2018

(65) Prior Publication Data

US 2019/0231509 A1    Aug. 1, 2019

(51) Int. Cl.
*A61F 2/04* (2013.01)
*A61B 17/12* (2006.01)
*A61M 39/24* (2006.01)
*A61F 2/24* (2006.01)

(52) U.S. Cl.
CPC .......... *A61F 2/04* (2013.01); *A61B 17/12104* (2013.01); *A61B 17/12172* (2013.01); *A61M 39/24* (2013.01); *A61B 17/12177* (2013.01); *A61F 2/24* (2013.01); *A61F 2002/043* (2013.01); *A61F 2220/0016* (2013.01); *A61F 2230/005* (2013.01); *A61F 2230/0093* (2013.01); *A61F 2240/00* (2013.01); *A61F 2250/0059* (2013.01); *A61M 2039/2433* (2013.01)

(58) Field of Classification Search
CPC ...... A61F 2/04; A61F 2/24; A61F 2230/0093; A61F 2002/043; A61F 2/82; A61B 17/12022; A61B 17/12027; A61B 17/12031; A61B 17/12036; A61B 17/1204; A61B 17/12045; A61B 17/12104; A61B 17/12172; A61M 39/24; A61M 2039/2433
See application file for complete search history.

(56) References Cited

U.S. PATENT DOCUMENTS

| | | | |
|---|---|---|---|
| 7,011,094 B2* | 3/2006 | Rapacki | A61B 17/12022 128/200.24 |
| 7,434,578 B2* | 10/2008 | Dillard | A61B 17/12104 128/200.24 |
| 2007/0232992 A1* | 10/2007 | Kutsko | A61B 17/12022 604/30 |
| 2009/0048480 A1* | 2/2009 | Klenk | A61B 17/00234 600/37 |
| 2012/0172927 A1* | 7/2012 | Campbell | A61B 17/0057 606/213 |
| 2016/0324641 A1 | 11/2016 | Solem | |
| 2018/0193618 A1* | 7/2018 | Erbey, II | A61F 2/00 |

* cited by examiner

*Primary Examiner* — Brian A Dukert
*Assistant Examiner* — Rebecca Lynee Zimmerman (57) ABSTRACT

A one-way valve device for blocking airflow in a lung passageway. The device includes a frame structure and a frameless membrane. The frame structure includes a hub and anchors. The frameless membrane attaches to the hub section. The anchors and the frameless membrane are at first radial positions in a closed configuration and at second radial positions in an open configuration. The first radial positions is closer to a central longitudinal axis of the device than the second radial positions. The frameless membrane includes a plurality of petals coupled to the base section. In the open configuration, the petals curve away from the central longitudinal axis of the one-way valve device. Proximal sections of the petals overlap proximal sections of adjacent petals when the one-way valve device is in the open or closed configurations.

6 Claims, 5 Drawing Sheets

REMOVABLE ANCHORED LUNG VOLUME REDUCTION DEVICES

BACKGROUND

Chronic obstructive pulmonary disease (COPD) has become a major cause of morbidity and mortality in the United States over the last three decades. COPD is characterized by the presence of airflow obstruction due to chronic bronchitis or emphysema. The airflow obstruction in COPD is due largely to structural abnormalities in the smaller airways. Important causes are inflammation, fibrosis, goblet cell metaplasia, and smooth muscle hypertrophy in terminal bronchioles.

The incidence, prevalence, and health-related costs of COPD are on the rise. Mortality due to COPD is also on the rise. In 1991, COPD was the fourth leading cause of death in the United States and had increased 33% since 1979. COPD affects the patient's whole life. It has three main symptoms: cough; breathlessness; and wheeze. At first, breathlessness may be noticed when running for a bus, digging in the garden, or walking uphill. Later, it may be noticed when simply walking in the kitchen. Over time, it may occur with less and less effort until it is present all of the time. COPD is a progressive disease and currently has no cure. Current treatments for COPD include the prevention of further respiratory damage, pharmacotherapy, and surgery. Each is discussed below.

The prevention of further respiratory damage entails the adoption of a healthy lifestyle. Smoking cessation is believed to be the single most important therapeutic intervention. However, regular exercise and weight control are also important. Patients whose symptoms restrict their daily activities or who otherwise have an impaired quality of life may require a pulmonary rehabilitation program including ventilatory muscle training and breathing retraining. Long-term oxygen therapy may also become necessary.

Pharmacotherapy may include bronchodilator therapy to open up the airways as much as possible or inhaled beta agonists. For those patients who respond poorly to the foregoing or who have persistent symptoms, ipratropium bromide may be indicated. Further, courses of steroids, such as corticosteroids, may be required. Lastly, antibiotics may be required to prevent infections and influenza and pneumococcal vaccines may be routinely administered. Unfortunately, there is no evidence that early, regular use of pharmacotherapy will alter the progression of COPD.

About 40 years ago, it was first postulated that the tethering force that tends to keep the intrathoracic airways open was lost in emphysema and that by surgically removing the most affected parts of the lungs, the force could be partially restored. Although the surgery was deemed promising, the lung volume reduction surgery (LVRS) procedure was abandoned. LVRS was later revived. In the early 1990s, hundreds of patients underwent the procedure. However, the procedure has fallen out of favor when Medicare stopped reimbursing for LVRS. Unfortunately, data is relatively scarce and many factors conspire to make what data exists difficult to interpret. The procedure is currently under review in a controlled clinical trial. However, what data does exist tends to indicate that patients benefited from the procedure in terms of an increase in forced expiratory volume, a decrease in total lung capacity, and a significant improvement in lung function, dyspnea, and quality of life. Improvements in pulmonary function after LVRS have been attributed to at least four possible mechanisms. These include enhanced elastic recoil, correction of ventilation/perfusion mismatch, improved efficiency of respiratory musculature, and improved right ventricular filling.

Lastly, lung transplantation is also an option. Today, COPD is the most common diagnosis for which lung transplantation is considered. Unfortunately, this consideration is given for only those with advanced COPD. Given the limited availability of donor organs, lung transplant is far from being available to all patients.

There is a need for additional non-surgical options for permanently treating COPD without surgery. A promising new therapy includes non-surgical apparatus and procedures for lung volume reduction by permanently obstructing the air passageway that communicates with the portion of the lung to be collapsed. The therapy includes placing an obstruction in the air passageway that prevents inhaled air from flowing into the portion of the lung to be collapsed. Lung volume reduction with concomitant improved pulmonary function may be obtained without the need for surgery. The effectiveness of obstructions may be enhanced if it is anchored in place. The effectiveness may also be enhanced if the obstruction is removable. However, no readily available apparatus and method exists for anchoring the obstruction, and for removal if required.

In view of the foregoing, there is a need in the art for a new and improved apparatus and method for permanently obstructing an air passageway that is anchored in place, and that may be removed if required.

SUMMARY

The present invention provides a one-way valve device that includes a frame structure and a frameless membrane component. The frame structure includes a hub section at a proximal end and a plurality of anchors at a distal end. The frameless membrane component includes a distal base section that attaches to at least a portion of the hub section. The one-way valve device transitions between a closed configuration and an open configuration. The anchors and the frameless membrane component are at first radial positions in the closed configuration and at second radial positions in the open configuration distance. The first radial positions being closer to a central longitudinal axis of the one-way valve device than the second radial positions.

In one aspect of the invention, the frameless membrane component includes a flexible, injection molded material. The injection molded material includes a plurality of petals. The petals include a base section that extends from the distal base section and a plurality of petals coupled to the base section.

In another aspect of the invention, when the one-way valve device is in the open configuration, the petals curve away from the central longitudinal axis of the one-way valve device from a distal end to a proximal end direction.

In still another aspect of the invention, a proximal section of at least one of the petals includes of a material or an amount of material configured to be more flexible than other sections of the at least one petal.

In yet another aspect of the invention, the proximal sections of the petals overlap proximal sections of adjacent petals when the one-way valve device is in the open or closed configurations.

In further another aspect of the invention, the one-way valve device includes a second frameless membrane component that includes a distal base section and a plurality of petals. The petals include a distal section connected to the distal base section of the second frameless membrane component. A gap exists between adjacent petals of the first frameless membrane when in the open configuration. A gap exists between adjacent petals of the second frameless membrane when in the open configuration. The petals of the second frameless membrane component overlap at least two the petals of the first frameless membrane component.

In still other aspects of the invention, the distal base section of the second frameless membrane component is attached to a more distal portion of the hub section than the distal section of the first frameless membrane component.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings.

DETAILED DESCRIPTION

Figure 1:
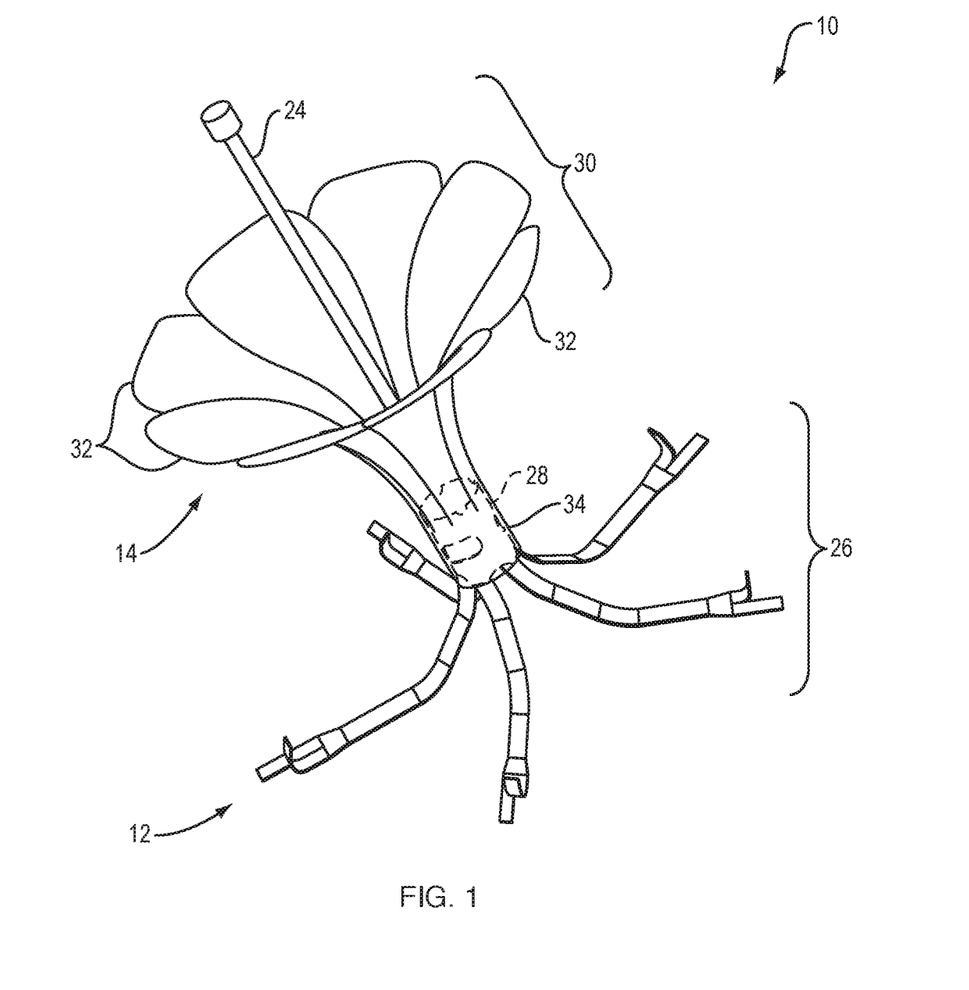
FIG. 1 shows a perspective view of a lung valve formed in accordance with an embodiment of the present invention.

As shown in FIG. 1, an exemplary lung valve 10 includes a frame structure 12, a sealing component 14 and a central rod 24. The frame structure 12 includes a hub 28 and one or more anchors 26. The sealing component 14 includes an expandable membrane section 30.

In one embodiment, the hub 28 and the anchors 26 are formed of a monolithic material, such as an etched hypotube. The anchors 26 extend from a distal end of the hub 28 and may include penetration limiters at the free ends of the anchors 26. The anchors 26 are connected at their proximal ends to a distal end of the hub 28.

The central rod 24 may be connected to the hub 28 by a weld joint, an adhesive and/or a pressure fitted joint. The central rod 24 extends proximally from the hub 28.

The membrane section 30 includes a base section 34 and a plurality of flexible membrane petals 32 that extend from the base section 34. Each of the flexible membrane petals 32 includes a proximal end having a first width value and a proximal end having a second width value. The first width value is greater than the second width value. The proximal ends of the petals 32 connect the base section 34. The first width value of the petals may not all be equal. The second width values of the petals may not all be equal.

The petals 32, when in an expanded configuration, bend away from the central rod 24 in the proximal direction. A proximal end of the central rod 24 is more proximal than the proximal end of the petals 32 whether in an expanded or compressed configuration. The central rod 24 is used by other tools to position, reposition or remove the lung valve 10.

The proximal ends of the petals 32 may have curved corners so that when the petals 32 are an expanded configuration a small gap exists between the corners of adjacent petals 32. In one embodiment, a portion of the proximal ends of the petals 32 are more flexible than the rest of the petals 32. The more flexible portion may be flexible enough to conform to a lumen wall when placed within a body lumen.

In one embodiment, the membrane section 30 is formed using an injection molding process. The material of the membrane section 30 and the shape of a die mold used to create the membrane section 30 causes the petals 32 to be biased in an open or expanded configuration. A diameter between the proximal edges of the petals 32 is greater than a diameter of the base section 34 when in the expanded configuration. The base section 34 is sized to fit over the hub 28. The base section 34 is pressure fitted over the hub 28 and/or attached to the exterior surface of the hub 28 by an adhesive and/or some latching mechanism. The membrane section 30 is formed of a flexible and strong shape memory material, which provides a seal of airflow in one direction and allows air to pass in the other direction. An example material is silicone, such as liquid silicone rubber (LSR) and high consistency silicone elastomers. Other petal shapes may be used provided they provide similar capabilities/qualities.

Figure 2:
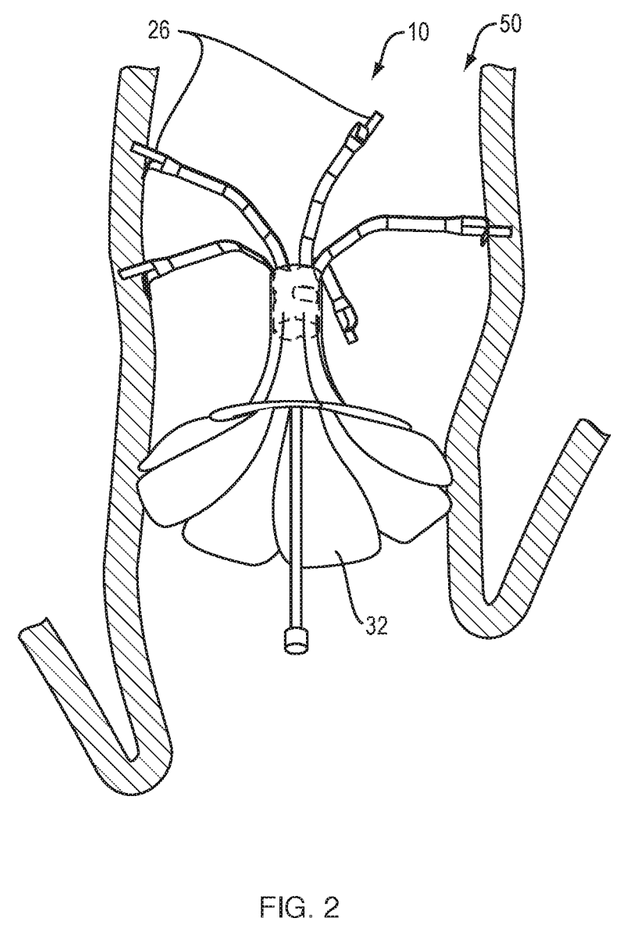
FIG. 2 shows the lung valve of FIG. 1 in an expanded configuration within an airway.

FIG. 2 illustrates a perspective view of the lung valve 10 shown within a cross-sectional view of airway 50. In this image, up is more distal within the airway 50 of the associated lung. When the lung valve 10 is within the airway 50 in the expanded configuration after release from a delivery catheter (not shown), the anchors 26 project radially to penetrate the walls of the lumen 50 distal from the location of the flexible membrane petals 32. The petals 32 cause the blockage of air due to inhalation (i.e., up (distal) as shown in FIG. 2). Inhalation air pressure pushes on inner surfaces of the petals 32 creating a distal or expansion force on the petals 32. The anchors 26 keep the lung valve 10 in place by combating the experienced forces. Also, any expansion of the petals 32 as a result of the created distal force would cause the petals 32 to expand more depending upon the petals stiffness, thus creating more of a seal with the wall of the lumen 50.

When the lung valve 10 experiences air pressure due to exhalation, the escaping air that is moving down (proximally) would pass by the anchors 26 and make contact with outer surfaces of the petals 32. The exhaled air pressure may cause the petals 32 to contract or compress depending upon petal stiffness, so that air may pass proximally by the petals 32. Contraction may also allow for mucociliary transport out of the airway in the proximal direction. The petals 32 may be strengthened in order to limit the amount contraction or expansion during the breathing cycles.

Figure 3:
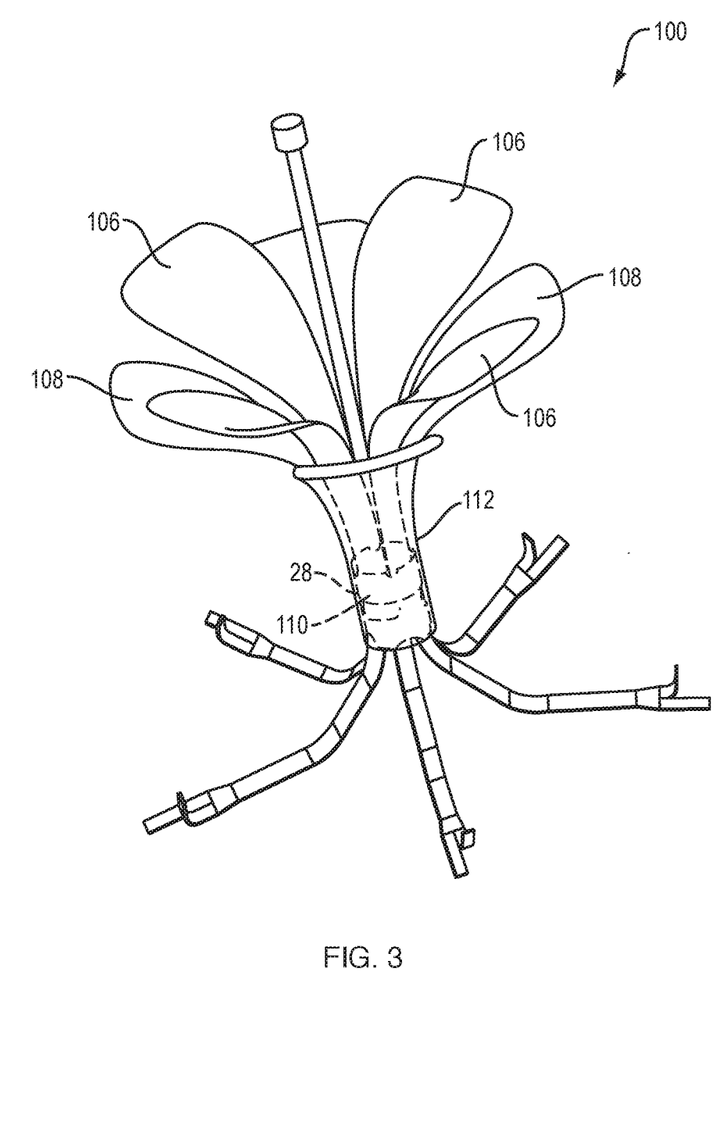
FIG. 3 is a perspective view of an alternate embodiment of a lung valve formed in accordance with an embodiment of the present invention.

In one embodiment, FIG. 3, illustrates an exemplary lung valve 100 that includes a proximal set of petals 106 and a distal set of petals 108. Each of the set of petals 106, 108 are created through separate injection molding processes, but could use the same die. The proximal set of petals 106 include a base section 110 that attaches to and/or is pressure fitted around a proximal portion of the hub 28. The distal set of petals 108 include a base section 112 that attaches to and/or is pressure fitted around a distal portion of the hub 28. The base section 112 of the distal set of petals 108 may be attached to and/or pressure fitted around the base section 110 of the proximal set of petals 106.

In one embodiment, the petals 106, 108 are of equal length, however, when positioned on the hub 28, as described above, the proximal ends of the petals 106 will be more proximal than the proximal ends of the petals 108. In one embodiment, the petals 106, 108 are not of equal length, but when the petals 106, 108 are mounted to the hub 28, as shown in FIG. 3 and described above, the proximal ends of the petals 106, 108 will be collocated longitudinally.

The proximal set of petals 106 include 4 equally spaced petals and the distal set of petals 108 also includes 4 equally spaced petals. When the lung valve 100 is in the expanded configuration, the proximal ends of the petals of the proximal set of petals 106 do not overlap with adjacent petals of the proximal set of petals 106. Also, when the lung valve 100 is in the expanded configuration, the proximal ends of the petals of the distal set of petals 108 do not overlap with adjacent petals of the proximal set of petals 108. The petals of the proximal set of petals 106 are offset by a predefined angular value from the petals of the distal set of petals 108. The predefined angular values may be within any of a number ranges (e.g., 75°-105°), such that the petals of the distal set of petals 108 cover at least gaps created between adjacent petals of the proximal set of petals 106. Any number of may be used provided that they provide the proper seal and can be compressed for delivery.

Figure 4:
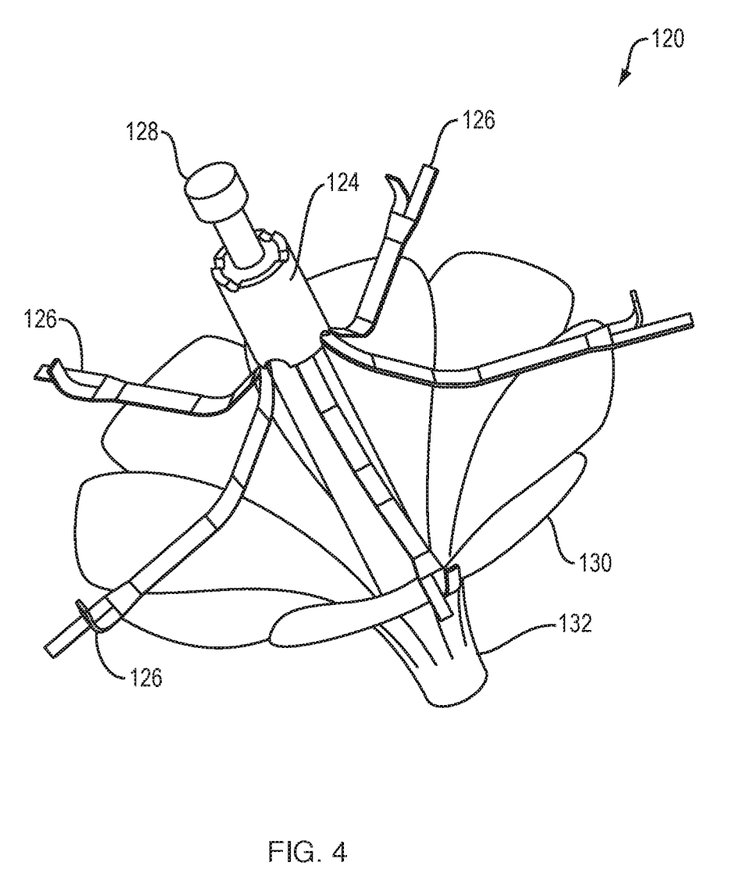
FIG. 4 is a perspective view of an alternate embodiment of a lung valve formed in accordance with an embodiment of the present invention.

In one embodiment, FIG. 4 illustrates a lung valve 120 that includes a set of anchors 126 attached to a hub 124 that is proximal from the anchors 126. The hub 124 is attached to or slidably received at or near a proximal end of a central hub 128. A distal end of the central hub 128 receives a base 132 of a set of petals 130. In a closed configuration, the petals 130 close closest to the center hub 128 with the anchors 126 located more distant radially from the center hub 128. The petals 130 may be configured similar to what is shown and/or described above.

Figure 5:
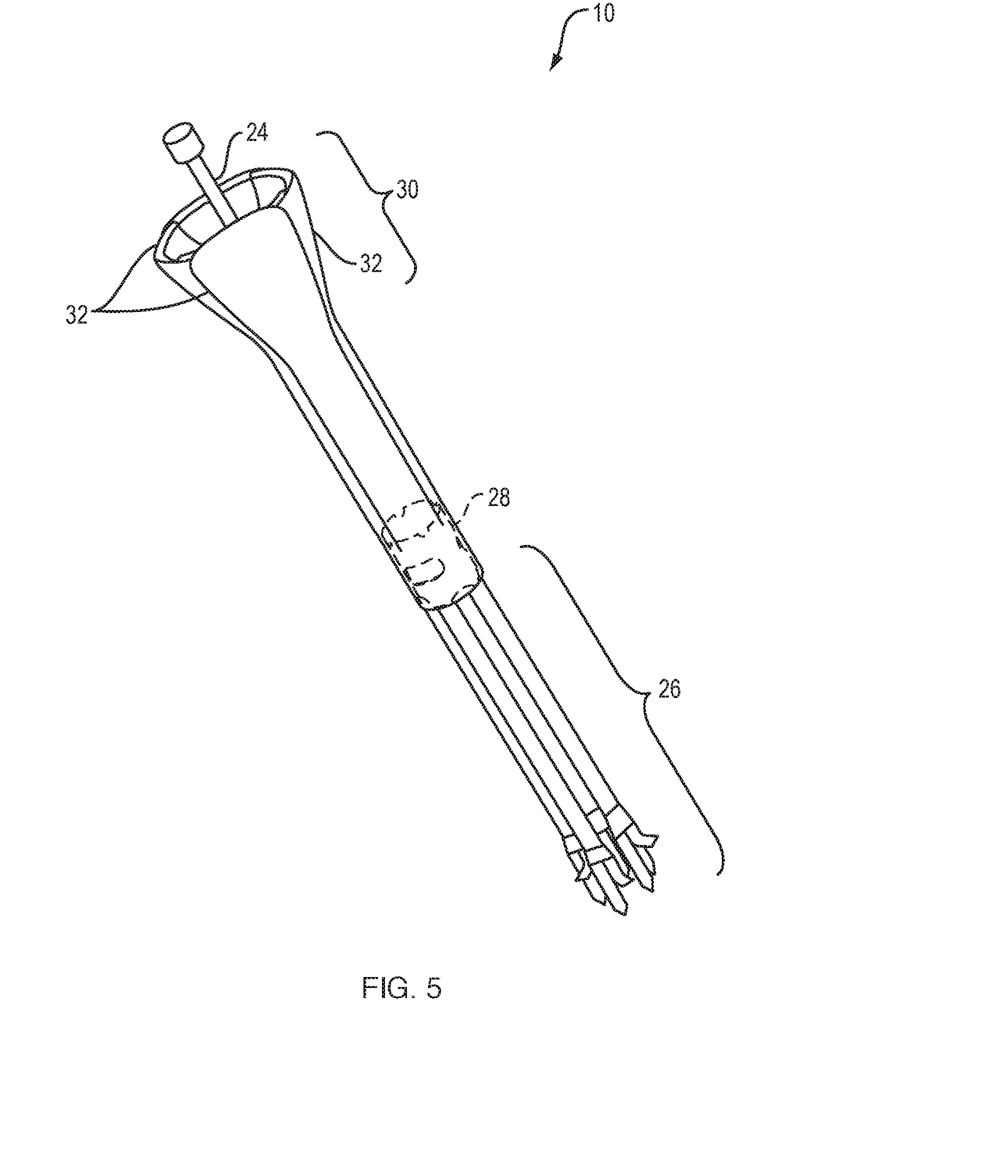
FIG. 5 is side view of the lung valve of FIG. 1 in a closed configuration.

FIG. 5 shows the valve 10 in a closed configuration. In the closed configuration the valve 10 may be loaded in a bronchoscope or a delivery catheter for transporting to a desired location in a lung.

Embodiments

A. A one-way valve device comprising: a frame structure comprising: a hub section at a proximal end; and a plurality of anchors at a distal end; and a frameless membrane component comprising a distal base section configured to be attached to at least a portion of the hub section, wherein the one-way valve device is configured to transition between a closed configuration and an open configuration, wherein the anchors and the frameless membrane component are at first radial positions in the closed configuration and at second radial positions in the open configuration, the first radial positions being closer to a central longitudinal axis of the one-way valve device than the second radial positions.

B. The device of A, wherein the frameless membrane component comprises a flexible, injection molded material.

C. The device of B, wherein the injection molded material comprises a plurality of petals, the petals comprising: a base section that extends from the distal base section; and a plurality of petals coupled to the base section.

D. The device of any of A-C, wherein when the one-way valve device is in the open configuration, the petals curve away from the central longitudinal axis of the one-way valve device from a distal end to a proximal end.

E. The device of D, wherein a proximal section of at least one of the petals comprises at least one of a material or an amount of material configured to be more flexible than other sections of the at least one petal.

F. The device of any of D or E, wherein proximal sections of the petals overlap proximal sections of adjacent petals when the one-way valve device is in the open or closed configurations.

G. The device of any of D or E, further comprising a second frameless membrane component comprising: a distal base section; and a plurality of petals comprising a distal section connected to the distal base section of the second frameless membrane component, wherein a gap exists between adjacent petals of the first frameless membrane when in the open configuration, wherein a gap exists between adjacent petals of the second frameless membrane when in the open configuration, wherein the petals of the second frameless membrane component overlap at least two the petals of the first frameless membrane component.

H. The device of G, wherein the distal base section of the second frameless membrane component is attached to a more distal portion of the hub section than the distal the base section of the first frameless membrane component.

I. The device of any of A-H, further comprising a central rod having a distal end attached to an inner surface of the hub section.

J. A one-way valve device comprising: a frame structure comprising: a hub section at a proximal end; and a plurality of anchors at a distal end; a central rod comprising: longitudinal axis; a proximal end; and a distal end, wherein the central rod being configured to receive the hub section at the proximal end; and a frameless membrane component comprising a distal base section configured to be attached to the distal end of the central rod, wherein the one-way valve device is configured to transition between a closed configuration and an open configuration, wherein the anchors and the frameless membrane component are at first radial positions in the closed configuration and at second radial positions in the open configuration distance, the first radial positions being closer to the longitudinal axis of the central rod than the second radial positions.

K. The device of J, wherein the frameless membrane component comprises a flexible, injection molded material.

L. The device of K, wherein the injection molded material comprises a plurality of petals, the petals comprising: a base section that extends from the distal base section; and a plurality of petals coupled to the base section.

M. The device of K, wherein when the one-way valve device is in the open configuration, the petals curve away from the central longitudinal axis of the one-way valve device from a distal end to a proximal end.

N. The device of any of L or M, wherein a proximal section of at least one of the petals comprises at least one of a material or an amount of material configured to be more flexible than other sections of the at least one petal.

O. The device of any of L-N, wherein proximal sections of the petals overlap proximal sections of adjacent petals when the one-way valve device is in the open or closed configurations.

P. The device of any of L-N, further comprising a second frameless membrane component comprising: a distal base section; and a plurality of petals comprising a distal section connected to the distal base section of the second frameless membrane component, wherein a gap exists between adjacent petals of the first frameless membrane when in the open configuration, wherein a gap exists between adjacent petals of the second frameless membrane when in the open configuration, wherein the petals of the second frameless membrane component overlap at least two the petals of the first frameless membrane component.

Q. The device of P, wherein the distal base section of the second frameless membrane component is attached to a more distal portion of the distal end of the central rod than the distal base section of the first frameless membrane component.

The description of the invention is merely exemplary in nature and variations that do not depart from the gist of the invention are intended to be within the scope of the invention. Such variations are not to be regarded as a departure from the spirit and scope of the invention.

Although the preferable embodiments of the present invention have been described hitherto, the present invention is not limited to these embodiments. Additions, omissions, substitutions, and other modifications can be made without departing from the spirit or scope of the present invention.

In addition, the invention is not limited by the above description and is limited by only the scope of appended claims.

What is claimed is:

1. A one-way valve device comprising:
a frame structure comprising:
a hub section at a proximal end; and
a plurality of anchors at a distal end; and
a one-way valve component comprising a frameless membrane component, the frameless membrane component comprising a distal base section configured to be attached to at least a portion of the hub section,
wherein the one-way valve device is configured to transition between a closed configuration and an open configuration,
wherein the anchors and the frameless membrane component are at first radial positions in the closed configuration and at second radial positions in the open configuration, the first radial positions being closer to a central longitudinal axis of the one-way valve device than the second radial positions
wherein the frameless membrane component comprises a flexible, injection molded material, the injection molded material comprises a plurality of petals, the petals comprising:
a base section that extends from the distal base section; and
a plurality of petals coupled to the base section,
wherein when the one-way valve device is in the open configuration, the petals curve away from the central longitudinal axis of the one-way valve device from a distal end to a proximal end,
wherein a proximal section of at least one of the petals comprises at least one of a material or an amount of material configured to be more flexible than other sections of the at least one proximal petal.

2. A one-way valve device comprising:
a frame structure comprising:
a hub section at a proximal end; and
a plurality of anchors at a distal end; and
a one-way valve component comprising a frameless membrane component and a second frameless membrane, the frameless membrane component comprising a distal base section configured to be attached to at least a portion of the hub section,
wherein the one-way valve device is configured to transition between a closed configuration and an open configuration,
wherein the anchors and the frameless membrane component are at first radial positions in the closed configuration and at second radial positions in the open configuration, the first radial positions being closer to a central longitudinal axis of the one-way valve device than the second radial positions
wherein the frameless membrane component comprises a flexible, injection molded material, wherein the injection molded material comprises a plurality of petals, the petals comprising:
a base section that extends from the distal base section; and
a plurality of petals coupled to the base section,
wherein when the one-way valve device is in the open configuration, the petals curve away from the central longitudinal axis of the one-way valve device from a distal end to a proximal end,
wherein the second frameless membrane component comprising:
a distal base section; and
a plurality of petals comprising a distal section connected to the distal base section of the second frameless membrane component,
wherein a gap exists between adjacent petals of the first frameless membrane when in the open configuration,
wherein a gap exists between adjacent petals of the second frameless membrane when in the open configuration,
wherein the petals of the second frameless membrane component overlap at least two of the petals of the first frameless membrane component.

3. The device of claim 2, wherein the distal base section of the second frameless membrane component is attached to a more distal portion of the hub section than the distal base section of the first frameless membrane component.

4. The device of claim 1, further comprising a central rod having a distal end attached to an inner surface of the hub section.

5. A one-way valve device comprising:
a frame structure comprising:
a hub section at a proximal end; and
a plurality of anchors at a distal end;
a central rod comprising:
a longitudinal axis;
a proximal end; and
a distal end,
wherein the central rod being configured to receive the hub section at the proximal end; and
a frameless membrane component comprising a distal base section configured to be attached to the distal end of the central rod,
wherein the one-way valve device IS configured to transition between a closed configuration and an open configuration,
wherein the anchors and the frameless membrane component are at first radial positions in the closed configuration and at second radial positions in the open configuration distance, the first radial positions being closer to the longitudinal axis of the central rod than the second radial positions,
wherein the frameless membrane component comprises a flexible, injection molded material, the injection molded material comprises a plurality of petals, the petals comprising:
a base section that extends from the distal base section; and
a plurality of petals coupled to the base section, wherein when the one-way valve device is in the open configuration, the petals curve away from the central longitudinal axis of the one-way valve device from a distal end to a proximal end wherein a proximal section of at least one of the petals comprises at least one of a material or an amount of material configured to be more flexible than other sections of the at least one petal.

6. The device of claim 2, wherein proximal sections of the petals overlap proximal sections of adjacent petals when the one-way valve device is in the open or closed configurations.

\* \* \* \* \*